United States Patent
Ishihara et al.

(10) Patent No.: US 6,770,265 B2
(45) Date of Patent: Aug. 3, 2004

(54) TOOTH SURFACE TREATMENT MATERIAL AND TOOTH SURFACE TREATMENT METHOD

(75) Inventors: Yoko Ishihara, Tokyo (JP); Eiichi Yoshii, Tokyo (JP)

(73) Assignee: GC Corporation, Tokyo (JP)

( * ) Notice: Subject to any disclaimer, the term of this patent is extended or adjusted under 35 U.S.C. 154(b) by 15 days.

(21) Appl. No.: 10/209,934

(22) Filed: Aug. 2, 2002

(65) Prior Publication Data

US 2003/0064035 A1 Apr. 3, 2003

(30) Foreign Application Priority Data

Sep. 28, 2001 (JP) ........................................ 2001-301767

(51) Int. Cl.$^7$ .............................. A61K 7/16; A61K 6/00
(52) U.S. Cl. ........................... 424/49; 424/57; 433/215; 433/216; 433/228.1; 106/35
(58) Field of Search ...................... 424/49–58; 433/215, 433/216, 228.1; 106/35

(56) References Cited

U.S. PATENT DOCUMENTS

| | | | | |
|---|---|---|---|---|
| 4,080,440 A | * | 3/1978 | DiGiulio et al. ............... | 424/57 |
| 4,083,955 A | * | 4/1978 | Grabenstetter ............... | 424/57 |
| 4,397,837 A | * | 8/1983 | Raaf et al. ..................... | 424/57 |
| 4,532,124 A | * | 7/1985 | Pearce ........................... | 424/57 |
| 5,234,971 A | * | 8/1993 | Imai et al. ..................... | 424/57 |
| 5,522,726 A | * | 6/1996 | Hodosh .................... | 433/228.1 |
| 5,534,244 A | * | 7/1996 | Tung ............................. | 424/57 |
| 5,603,922 A | * | 2/1997 | Winston et al. ............... | 424/57 |
| 5,874,066 A | * | 2/1999 | Hack et al. ............... | 433/228.1 |
| 5,879,663 A | * | 3/1999 | Nakabayashi et al. ......... | 424/57 |
| 5,895,641 A | * | 4/1999 | Usen et al. .................... | 424/57 |
| 5,906,809 A | * | 5/1999 | Hack et al. .............. | 433/228.1 |
| 6,485,708 B1 | * | 11/2002 | Winston et al. ............... | 424/57 |

* cited by examiner

*Primary Examiner*—Shep K. Rose
(74) *Attorney, Agent, or Firm*—Oblon, Spivak, McClelland, Maier & Neustadt, P.C.

(57) ABSTRACT

A tooth surface treatment material and method to eliminate a smear layer, to deliver an inorganic component of a tooth structure in a dental cavity to the tooth structure to make a glass ionomer cement firmly adhere particularly to a dentin which includes an aqueous solution containing 2~30% by weight of a water-soluble calcium salt and an acid which does not react with the calcium salt by ½ or less of the weight of the calcium salt and having a pH of 2 or less and an aqueous solution containing a water-soluble phosphate other than a calcium salt, or an aqueous solution containing 2~30% by weight of a water-soluble calcium salt and an aqueous solution containing 2~30% by weight of a water-soluble phosphate other than a calcium salt and an acid which does not react with the phosphate by ½ or less of the weight of the phosphate and having a pH of 2 or less, the acid-containing aqueous solution being first applied, and the other solution being subsequently applied onto the teeth surface.

10 Claims, No Drawings

TOOTH SURFACE TREATMENT MATERIAL AND TOOTH SURFACE TREATMENT METHOD

BACKGROUND OF THE INVENTION

1. Field of the Invention

The present invention relates to a tooth surface treatment material and a tooth surface treatment method for treating a dental cavity during undergoing restorative for a deficient part of a tooth structure in the dental therapy. More particularly, the present invention relates to a tooth surface treatment material and a tooth surface treatment method for more enhancing and stabilizing an adhesive force between a glass ionomer cement and a tooth structure within a dental cavity.

2. Description of the Related Art

In the present dental therapy is usually employed a restorative in which a dental caries part is cut to form a cavity by using a diamond point, etc., and the thus formed cavity is filled with a filling material such as a glass ionomer cement and a composite resin. If such filling material does not firmly adhere to a tooth structure within a dental cavity, the filling material comes off so that a patient must take again the therapy. Alternatively, even if the filling material does not come off, when a gap is present, there is a high possibility to generate a crisis of secondary dental caries. Accordingly, relative merits of the adhesion between the filling material and the tooth structure within the dental cavity is one of the important factors in clinching the restorative.

However, when the tooth is cut to form a cavity, its cutting wastes, saliva, etc. are rubbed on the tooth surface to form a smear layer having a thickness of 1~5 $\mu$m. This smear layer cannot be eliminated by water, hydrogen peroxide, etc. When the smear layer is present between various filling materials and the tooth structure within the dental cavity, the adhesion becomes very instable, possibly resulting in decrease in and scattering of the adhesive force.

As a method for eliminating the smear layer, there has hitherto been used an acid-etching method using a phosphoric acid solution of 30~60% by weight. This method that a tooth surface within a dental cavity is treated with a phosphoric acid solution for a predetermined period of time to dissolve a smear layer therein and then rinsed with water to eliminate the smear layer. In the case where the tooth structure cut is of an inorganic component-rich enamel, after eliminating the smear layer by phosphoric acid-etching, a glass ionomer cement is filled, an improving effect of the adhesive force is observed. However, since the glass ionomer cement exhibits adhesive properties to the tooth structure by bonding between the inorganic component in the tooth structure and a carboxyl group of the glass ionomer cement, in an inorganic component-poor dentin, the healthy dentin is also demineralized by the phosphoric acid-etching. In this case, when the inorganic component is lost, the adhesive force was likely lowered.

Thus, there was required a tooth surface treatment material that can eliminate the smear layer so that the glass ionomer cement can obtain a strong adhesive force to the tooth structure within the dental cavity and is able to feed the inorganic component to the tooth structure.

In order to meet such require, West German Laid-Open Patent OLS No. 2,452,969 discloses a method in which a first solution is prepared as a solution of a water-soluble calcium salt of 0.005~5% having a pH of less than 5, a second solution is prepared as a solution of a water-soluble phosphate of 0.005~5% having a pH of 2.5~4, and the first solution and the second solution are mixed to prepare a solution having a pH of from 2 to 5, which is then applied onto a tooth surface. According to this method, since the solution prepared by mixing the two solutions is low in acidity being pH 2~5, it takes a long period of time to eliminate the smear layer. Also, since the mixed solution is applied onto the tooth surface after mixing the calcium component in the first solution and the phosphoric acid component in the second solution, prior to the contact with the tooth surface a calcium ion and a phosphoric acid ion are already reacted with each other to form a crystal. Accordingly, the penetration properties of the calcium ion and the phosphoric acid ion into the interior of the tooth structure are poor, and the reactant only accumulates on the tooth surface, so that an improvement in the adhesive force between the glass ionomer cement and the tooth structure within the dental cavity cannot be expected.

Further, JP-B-86367/1994 titled "TREATING AGENT OF TOOTH SURFACE" discloses a treating agent of tooth surface for treating an enamel surface and/or a dentin surface, which consists of 5~50% by weight of an organic carboxylic acid or an anhydride thereof, 5~50% by weight of calcium chloride, and water. According to this treating agent of tooth surface, the smear layer can be eliminated, and the calcium ion can be made to penetrate into the tooth structure. However, the calcium ion is only dissolved in the penetration solution. When a time elapses, the calcium ion is taken into a body, so that an effect for keeping the adhesion between the glass ionomer cement and the tooth structure within the dental cavity over a long period of time cannot be expected.

SUMMARY OF THE INVENTION

The present invention is aimed to overcome the above-described defects of the related art and to provide a tooth surface treatment material and a tooth surface treatment method capable of eliminating a smear layer, delivering an inorganic component of a tooth structure within a dental cavity to the tooth structure, and making a glass ionomer cement firmly adhere particularly to a dentin.

The present inventor has made extensive and intensive investigations in order to achieve the above-described aim. As a result, it has been found that with respect to a tooth surface treatment material comprising an aqueous solution containing 2~30% by weight of a water-soluble calcium salt and an acid which does not react with the water-soluble calcium salt so as not to form a compound in an amount of ½ or less of the weight of the water-soluble calcium salt and having a pH of 2 or less, and another aqueous solution containing from 2 to 30% by weight of a water-soluble phosphate other than a calcium salt, and a tooth surface treatment material comprising an aqueous solution containing 2~30% by weight of a water-soluble calcium salt and another aqueous solution containing 2~30% by weight of a water-soluble phosphate other than a calcium salt and an acid which does not react with the water-soluble phosphate so as not to form a compound in an amount of ½ or less of the weight of the water-soluble phosphate and having a pH of 2 or less, when the acid-containing aqueous solution is first applied onto a tooth surface, not only a smear layer can be dissolved by the acid, but also the water-soluble calcium salt or the water-soluble phosphate other than a calcium salt contained in the acid-containing aqueous solution can be delivered to a tooth structure within a dental cavity; when the other aqueous solution not containing an acid is subsequently applied onto the tooth structure, the water-soluble phosphate other than a calcium salt or the water-soluble calcium salt contained in the other aqueous solution is delivered to the tooth structure and reacts with the water-soluble calcium salt or the water-soluble phosphate other than a calcium salt as previously delivered to the tooth structure to form a compound, so that when the tooth surface is then rinsed with water, though the smear layer is eliminated, the inorganic component delivered to the tooth structure remains on the tooth structure, thereby enabling to improve and stabilize an adhesive force between a glass ionomer cement and the tooth structure, leading to accomplishment of the present invention.

Specifically, the present invention is to provide a tooth surface treatment material comprising an aqueous solution containing 2~30% by weight of a water-soluble calcium salt and an acid which does not react with the water-soluble calcium salt so as not to form a compound in an amount of ½ or less of the weight of the water-soluble calcium salt and having a pH of 2 or less and another aqueous solution containing 2~30% by weight of a water-soluble phosphate other than a calcium salt, wherein the tooth surface treatment material is used in such a manner that the acid-containing aqueous solution is first applied onto a tooth surface, and the other aqueous solution is subsequently applied onto the teeth surface, and a tooth surface treatment method using the same; and a tooth surface treatment material comprising another aqueous solution containing 2~30% by weight of a water-soluble calcium salt and an aqueous solution containing 2~30% by weight of a water-soluble phosphate other than a calcium salt and an acid which does not react with the water-soluble phosphate so as not to form a compound in an amount of ½ or less of the weight of the water-soluble phosphate and having a pH of 2 or less, wherein the tooth surface treatment material is used in such a manner that the acid-containing aqueous solution is first applied onto a tooth surface, and the other aqueous solution is subsequently applied onto the teeth surface, and a tooth surface treatment method using the same.

In the tooth surface treatment materials, it is preferred that the aqueous solution containing 2~30% by weight of a water-soluble phosphate other than a calcium salt further contains 0.0001~3% by weight of a water-soluble fluoride; that the aqueous solution containing 2~30% by weight of a water-soluble phosphate other than a calcium salt and an acid which does not react with the water-soluble phosphate so as not to form a compound in an amount of ½ or less of the weight of the water-soluble phosphate and having a pH of 2 or less further contains 0.0001~3% by weight of a water-soluble fluoride; that the water-soluble fluoride is at least one selected from a group consisting of potassium fluoride, sodium fluoride, and nickel fluoride sodium monofluorophosphate; that the water-soluble calcium salt is at least one selected from a group consisting of calcium chloride, calcium nitrate, calcium bromide, and calcium dihydrogenphosphate; that the water-soluble phosphate is at least one selected from a group consisting of dipotassium hydrogenphosphate, disodium hydrogenphosphate, and dilithium hydrogenphosphate; and that the acid is at least one selected from a group consisting of phosphoric acid, maleic acid, and maleic anhydride.

DETAILED DESCRIPTION OF THE INVENTION

As the water-soluble calcium salt that is used for the tooth surface treatment material and the tooth surface treatment method according to the present invention are employable water-soluble calcium salts which have hitherto been used for tooth surface treatment materials and remineralization materials. Specific examples include calcium chloride, calcium nitrate, calcium bromide, calcium propionate, calcium glycerophosphate, calcium gluconate, calcium lactate, calcium dihydrogenphosphate, and calcium pantothenate, among these, calcium chloride, calcium nitrate, calcium bromide, and calcium dihydrogenphosphate being preferred. These calcium salts can be used singly or in admixture of more than two thereof. A suitable content of the water-soluble calcium salt is 2~30% by weight. When the content of the water-soluble calcium salt is less than 2% by weight, the amount of the compound formed is too low when the two kinds of the aqueous solutions constituting the tooth surface treatment material according to the present invention is applied onto the tooth surface within the dental cavity, whereby an improvement in the adhesive force of the glass ionomer cement to the tooth surface within the dental cavity cannot be expected. On the other hand, when it exceeds 30% by weight, an excess of the compound is formed on the tooth surface within the dental cavity, so that the adhesive force of the glass ionomer cement to the tooth surface within the dental cavity is likely to be lowered. A preferred content of the water-soluble calcium salt is 5~20% by weight.

As the water-soluble phosphate other than a calcium salt, which is used for the tooth surface treatment material and the tooth surface treatment method according to the present invention, are employable water-soluble phosphates other than a calcium salt, which have hitherto been used for tooth surface treatment materials and remineralization materials. Specific examples include sodium dihydrogenphosphate, disodium hydrogenphosphate, trisodium phosphate, potassium dihydrogenphosphate, dipotassium hydrogenphosphate, tripotassium phosphate, lithium dihydrogenphosphate, trilithium phosphate, barium dihydrogenphosphate, barium hydrogenphosphate, magnesium dihydrogenphosphate, magnesium hydrogenphosphate, ammonium dihydrogenphosphate, diammonium hydrogenphosphate, disodium dihydrogen pyrophosphate, tetrasodium pyrophosphate, and tetrapotassium pyrophosphate. Of these, disodium hydrogenphosphate, dipotassium hydrogenphosphate, and dilithium hydrogenphosphate are preferred because they have a high affinity with living bodies. These phosphates can be used singly or in admixture of more than two thereof. A suitable content of the water-soluble phosphate other than a calcium salt is 2~30% by weight. When the content of the water-soluble phosphate other than a calcium salt is less than 2% by weight, the amount of the compound formed is too low when the two kinds of the aqueous solutions constituting the tooth surface treatment material according to the present invention is applied onto the tooth surface within the dental cavity, whereby an improvement in the adhesive force of the glass ionomer cement to the tooth surface within the dental cavity cannot be expected. On the other hand, when it exceeds 30% by weight, an excess of the compound is formed on the tooth surface within the dental cavity, so that the adhesive force of the glass ionomer cement to the tooth surface within the dental cavity is likely to be lowered. A preferred content of the water-soluble calcium salt is 5~20% by weight.

In the tooth surface treatment material and the tooth surface treatment method according to the present invention, when a water-soluble fluoride is contained in the aqueous solution containing 2~30% by weight of the water-soluble phosphate other than a calcium salt, or the aqueous solution containing 2~30% by weight of the water-soluble phosphate other than a calcium salt and an acid which does not react with the water-soluble phosphate so as not to form a compound in an amount of ½ or less of the weight of the water-soluble phosphate and having a pH of 2 or less, the water-soluble fluoride can be delivered to the tooth structure within the dental cavity, whereby the reaction between the water-soluble calcium salt and the water-soluble phosphate other than a calcium salt is accelerated by the water-soluble fluoride, and the formed compound has a composition similar to a fluoroapatite close to an inorganic component of a natural tooth structure, therefore, such being preferred. As the water-soluble fluoride are employable water-soluble fluorides which have hitherto been used for tooth surface treatment materials and remineralization materials. Specific examples include aluminium fluoride, antimony fluoride, ammonium fluoride, potassium fluoride, sodium fluoride, nickel fluoride, barium fluoride, manganese fluoride, and lithium fluoride, among these, potassium fluoride, sodium fluoride sodium monofluorophosphate, and nickel fluoride sodium monofluorophosphate being preferred. These fluorides can be used singly or in admixture of more than two thereof. A suitable content of the water-soluble fluoride is 0.0001~3% by weight. When the content of the water-soluble fluoride is less than 0.0001% by weight, an effect for accelerating the reaction between the water-soluble calcium salt and the water-soluble phosphate other than a calcium salt is difficult to obtain. On the other hand, when it exceeds 3% by weight, not only an excess of the compound is formed on the tooth surface within the dental cavity, so that the adhesive force of the glass ionomer cement to the tooth surface within the dental cavity is likely to be lowered, but also when a person accidentally drinks the thus formulated tooth surface treatment material, a danger to the living body increases, therefore, such is not preferred. A preferred content of the water-soluble fluoride is 0.005~1.5% by weight.

As the acid that is used for the tooth surface treatment material and the tooth surface treatment method according to the present invention are employable any acids so far as they does not react with the water-soluble calcium salt or the water-soluble phosphate other than calcium salt so as not to form a compound. For example, the following acids and anhydrides thereof can be enumerated. These include partial salts thereof. Specific examples include formic acid, acetic acid, lactic acid, butyric acid, valeric acid, nonanoic acid, hexanoic acid, heptanoic acid, lauric acid, pyruvic acid, benzoic acid, aminobenzoic acid, salicylic acid, aminosalicylic acid, oxalic acid, succinic acid, tartaric acid, glutaric acid, fumaric acid, maleic acid, malonic acid, citraconic acid, itaconic acid, phthalic acid, citric acid, ethylenediaminetetraacetic acid, acrylic acid, hydrochloric acid, sulfuric acid, nitric acid, carbonic acid, phosphoric acid, and perchloric acid, among these, citric acid, succinic acid, oxalic acid, tartaric acid, maleic acid, phosphoric acid, succinic anhydride, and maleic anhydride being preferred. In the case of phosphoric acid, maleic acid, or maleic anhydride, since it is hardly contained in the formed compound, the compound has a composition close to that of an inorganic component of a tooth. Accordingly, they are particularly preferred. These acid components can be used singly or in admixture of more than two thereof.

The content of the acid is in an amount of ½ or less of the weight of the water-soluble calcium salt or the water-soluble phosphate other than a calcium salt contained in the acid-containing aqueous solution and the pH of the aqueous solution is 2 or less. When the content of the acid is so low that unless the pH of the aqueous solution become 2 or less, it takes a long period of time to eliminate the smear layer. On the other hand, when the content of the acid exceeds ½ of the weight of the water-soluble calcium salt or the water-soluble phosphate other than a calcium salt simultaneously contained in the acid-containing aqueous solution, the compound formed when the two kinds of the aqueous solutions constituting the tooth surface treatment material according to the present invention is applied onto the tooth surface within the dental cavity contains the acid to excess, whereby the formulated tooth surface treatment material becomes instable, therefore, such being not preferred.

To adjust a pH of the aqueous solution having a pH of 2 or less, ingredients of another aqueous solution can be added to it as long as the ingredients are dissolves in it completely.

It is preferable that the two aqueous solutions are colored so as to be distinguished easily. Possible use may be made of various coloring materials, among which food dyes are preferred for the present invention, because they are harmless to the human body. Specific examples include Food Red No. 2, Food Red No. 3, Food Red No. 40, Food Red No. 102, Food Red No. 104, Food Red No. 105, Food Red No. 106, Food Yellow No. 4, Food Yellow No. 5, Food Blue No. 1, Food Blue No. 2, Food Green No. 3, Sodium iron chlorophyllin, Sodium copper chlorophyllin, Alkaline aqueous solution of annatto. These food dyes can be used in combination of two or more as well as separately. The quantity of the food dyes used preferably ranges from 0.001% by weight to 5% by weight. At less than 0.0001% by weight, the desired object is not attained because the two aqueous solutions are pale in color. On the other hand, when the food dye is used in excess of 5% by weight, tooth structure may possibly remain colored even upon washed with water. The bonding strength of the glass ionomer cement to tooth structure is rather decreased.

Incidentally, for the purpose of preventing the compound formed when the two kinds of the aqueous solutions constituting the tooth surface treatment material according to the present invention are applied onto the tooth surface within the dental cavity is again dissolved in an acidic atmosphere, sodium hydroxide, potassium hydroxide, or the like may be contained in the aqueous solution not containing an acid so that, when equal amounts of the two kinds of the aqueous solutions constituting the tooth surface treatment material according to the present invention are mixed with each other, the solution may have a pH of 2~7.

The tooth surface treatment method according to the present invention is carried out in the following manner. That is, in the tooth surface treatment material comprising an aqueous solution containing 2~30% by weight of a water-soluble calcium salt and an acid which does not react with the water-soluble calcium salt so as not to form a compound in an amount of ½ or less of the weight of the water-soluble calcium salt and having a pH of 2 or less and an aqueous solution containing 2~30% by weight of a water-soluble phosphate other than a calcium salt, or the tooth surface treatment material comprising an aqueous solution containing 2~30% by weight of a water-soluble calcium salt and an aqueous solution containing 2~30% by weight of a water-soluble phosphate other than a calcium salt and an acid which does not react with the water-soluble phosphate so as not to form a compound in an amount of ½ or less of the weight of the water-soluble phosphate and having a pH of 2 or less, the acid-containing aqueous solution is first applied onto a tooth surface. As a result, not only the smear layer can be dissolved by the acid contained in the aqueous solution, but also the water-soluble calcium salt or the water-soluble phosphate other than a calcium salt contained in the acid-containing aqueous solution can be delivered to a tooth structure. Subsequently, the other aqueous solution not containing an acid is applied onto the tooth structure. As a result, the water-soluble phosphate other than a calcium salt or the water-soluble calcium salt contained in the later applied aqueous solution is delivered to the tooth structure and reacts with the water-soluble calcium salt or the water-soluble phosphate other than a calcium salt as previously delivered to the tooth structure, to form a compound. Accordingly, when the tooth surface is then rinsed with water, though the smear layer is eliminated, the inorganic component delivered to the tooth structure remains on the tooth structure, thereby enabling to improve and stabilize the adhesion between the glass ionomer cement and the tooth structure within the dental cavity.

The present invention will be described below in detail with reference to the examples, however it should not be construed that the present invention is limited thereto.

(Preparation of Tooth Surface Treatment Material)

Solution A (an aqueous solution containing 2~30% by weight of a water-soluble calcium salt, or an aqueous solution containing 2 to 30% by weight of a water-soluble calcium salt and an acid which does not react with the water-soluble calcium salt so as not to form a compound in an amount of ½ or less of the weight of the water-soluble calcium salt and having a pH of 2 or less) and Solution B (an aqueous solution containing 2~30% by weight of a water-soluble phosphate other than a calcium salt, or an aqueous solution containing 2~30% by weight of a water-soluble phosphate other than a calcium salt and an acid which does not react with the water-soluble phosphate so as not to form a compound in an amount of ½ or less of the weight of the water-soluble phosphate and having a pH of 2 or less), each of which is used in Examples 1 to 7 and Comparative Examples 1 to 3, were prepared according to the formulation as shown in Table 1. Also, a tooth surface as just cut without being applied with any material was prepared as Comparative Example 4.

(Observation of Smear Layer)

A tooth root of bovine mandibular anterior teeth was cut off, and after extraction of pulp, a dentin was exposed using a diamond point. Thereafter, the bovine tooth dentin surface was dried by air, and a first solution was applied thereonto, and 40 seconds after the application of the first solution, a second solution was applied, each of the first and second solutions being prepared according to Examples 1 to 7 and Comparative Examples 1 to 3 as shown in Table 1. Forty seconds after the application of the second solution, the tooth surface was rinsed with distilled water, and the state of a smear layer was observed by means of a scanning electron microscope. The results obtained are summarized and shown in Table 1.

(Evaluation of Adhesive Properties)

A tooth root of bovine mandibular anterior teeth was cut off, and after extraction of pulp, a dentin was exposed using a #600 SiC paper. Thereafter, the bovine tooth dentin surface was dried by air, and a first solution was applied thereonto, and 40 seconds after the application of the first solution, a second solution was applied, each of the first and second solutions being prepared according to Examples 1 to 7 and Comparative Examples 1 to 3 as shown in Table 1. Forty seconds after the application of the second solution, the tooth surface was rinsed with distilled water and then dried by air. A masking tape provided with a hole having a diameter of 3 mm was stuck on the tooth surface, and a commercially available glass ionomer cement (Fuji IXGP, made by GC Corporation) was mixed and placed over the hole of the masking tape. Next, a stainless steel rod was pressed thereover from above and allowed to stand. After setting of the cement, the resulting sample was placed in a thermostatic chamber in temperature of 37° C. and humidity of 100%. Twenty-four hours and one week after the placement, the sample was measured for tensile adhesive strength at a crosshead speed of 1 mm/min. by means of a universal testing machine (a product name: Autograph, manufactured by Shimadzu Corporation). An average value and a standard deviation were obtained. The results obtained are summarized and shown in Table 1.

TABLE 1

(Preparation of tooth surface treatment material) (% by weight)

| | Ex. 1 | Ex. 2 | Ex. 3 | Ex. 4 | Ex. 5 | Ex. 6 | Ex. 7 | Ex. 8 | Com. Ex. 1 | Com. Ex. 2 | Com. Ex. 3 | Com. Ex. 4 |
|---|---|---|---|---|---|---|---|---|---|---|---|---|
| Application order of solution | A => B | A => B | A => B | A => B | A => B | B => A | B => A | A => B | A => B | Only A | Only A | |
| Solution A | | | | | | | | | | | | |
| Calcium chloride | 7 | | 10 | 15 | 22 | 15 | 7 | 10 | 10 | | 20 | |
| Calcium nitrate | | 28 | | 8 | | | | 5 | | | | |
| Calcium bromide | | | | | | | 3 | 5 | | | | |
| Dipotassium hydrogenphosphate | | | | | | | | | | | | |
| Succinic acid | 3 | | | | | | | | | | | |
| Phosphoric acid | | | 5 | | 8 | | | | | 30 | | |
| Maleic acid | | 9 | | 4 | | | | | | | | |
| Maleic anhydride | | 3 | | | | | | | | | | |
| Citric acid | | | | | | | | | | | 10 | |
| Potassium hydroxide | | | | | | | 0.05 | | | | | |
| Food Blue No. 1 | | | 0.0005 | | | | | | | | | |
| Distilled water | 90 | 60 | 84.9995 | 73 | 70 | 85 | 89.95 | 80 | 90 | 70 | 70 | |
| Solution B | | | | | | | | | | | | |
| Dipotassium hydrogenphosphate | | 30 | 12 | 10 | 3 | 20 | | 10 | | | | |
| Disodium hydrogenphosphate | 4 | | | 5 | 7 | | | | 4 | | | |
| Sodium dihydrogenphosphate | | | | | | | 7 | | 1 | | | |

TABLE 1-continued (Preparation of tooth surface treatment material) (% by weight)

| | Ex. 1 | Ex. 2 | Ex. 3 | Ex. 4 | Ex. 5 | Ex. 6 | Ex. 7 | Ex. 8 | Com. Ex. 1 | Com. Ex. 2 | Com. Ex. 3 | Com. Ex. 4 |
|---|---|---|---|---|---|---|---|---|---|---|---|---|
| Sodium fluoride | 0.03 | 0.8 | 0.1 | | | 1.5 | | 0.2 | 0.35 | | | |
| Potassium fluoride | | 0.5 | | | | | | | | | | |
| Phosphoric acid | | | | | | 10 | | | | | | |
| Maleic acid | | | | | | | 2 | | | | | |
| Sodium hydroxide | | | | | 0.5 | | | | | | | |
| Food Red No. 40 | 0.005 | | | | | | | | | | | |
| Distilled water | 95.965 | 68.7 | 87.9 | 85 | 89.5 | 68.5 | 91 | 89.8 | 94.65 | | | |
| Results | | | | | | | | | | | | |
| Elimination of smear layer | Yes | Yes | Yes | Yes | Yes | Yes | Yes | Yes | No | Yes | Yes | No |
| Adhesive strength (MPa): After 24 hours | 4.1 ± 0.5 | 4.5 ± 0.3 | 4.3 ± 0.2 | 4.0 ± 0.4 | 3.9 ± 0.6 | 3.7 ± 0.3 | 3.6 ± 0.4 | 4.8 ± 0.7 | 3.1 ± 1.2 | 3.2 ± 1.0 | 3.5 ± 1.5 | 3.0 ± 1.3 |
| Adhesive strength (MPa): After After 1 week | 4.0 ± 0.3 | 4.3 ± 0.2 | 4.2 ± 0.4 | 3.8 ± 0.5 | 3.8 ± 0.7 | 3.5 ± 0.5 | 3.4 ± 0.4 | 4.5 ± 0.6 | 2.8 ± 1.4 | 2.9 ± 1.1 | 2.4 ± 1.7 | 2.6 ± 1.6 |

Determination of elimination of smear layer:
Yes: Eliminated,
No: Not eliminated As is clear from Table 1, in Examples 1 to 7 using the tooth surface treatment material and the tooth surface treatment method according to the present invention, the smear layer was eliminated.

Also, with respect to the adhesive properties to the glass ionomer cement, as is clear from Table 1, it could be confirmed that in Examples 1 to 7 using the tooth surface treatment material according to the present invention, the adhesive strength is high, and the standard deviation is so small that a stable adhesive force is obtained, as compared with Comparative Examples 1 to 4.

As described above in detail, the tooth surface treatment material and the tooth surface treatment method according to the present invention are a tooth surface treatment material and a tooth surface treatment method, respectively, having extremely superior properties that a smear layer can be eliminated and that an inorganic component can be delivered to a tooth structure within a dental cavity, thereby enabling to firmly adhere a glass ionomer cement to the tooth structure. When a water-soluble fluoride is contained in an aqueous solution containing 2~30% by weight of a water-soluble phosphate other than a calcium salt, or an aqueous solution containing 2~30% by weight of a water-soluble phosphate other than a calcium salt and an acid which does not react with the water-soluble phosphate so as not to form a compound and having a pH of 2 or less, the water-soluble fluoride can be delivered to the tooth structure within the dental cavity, whereby the reaction between the water-soluble calcium salt and the water-soluble phosphate other than a calcium salt is accelerated by the water-soluble fluoride, and the formed compound has a composition similar to a fluoroapatite close to an inorganic component of a natural tooth structure. Therefore, the present invention is greatly valuable in contributing to the dental field.

While the present invention has been described in detail and with reference to specific embodiments thereof, it will be apparent to one skilled in the art that various changes and modifications can be made therein without departing from the spirit and scope thereof.

What is claimed is:

1. A tooth surface treatment material comprising an aqueous solution containing 2~30% by weight of a water-soluble calcium salt and an acid which does not react with the water-soluble calcium salt so as not to form a compound in an amount of ½ or less of the weight of the water-soluble calcium salt and having a pH of 2 or less and another aqueous solution containing 2~30% by weight of a water-soluble phosphate other than a calcium salt, wherein said tooth surface treatment material is used in such manner that said acid-containing aqueous solution is first applied onto a tooth surface, and the other aqueous solution is subsequently applied onto the teeth surface.

2. A tooth surface treatment material comprising an aqueous solution containing 2~30% by weight of a water-soluble calcium salt and another aqueous solution containing 2~30% by weight of a water-soluble phosphate other than a calcium salt and an acid which does not react with the water-soluble phosphate so as not to form a compound in an amount of ½ or less of the weight of the water-soluble phosphate and having a pH of 2 or less, wherein the tooth surface treatment material is used in such manner that the acid-containing aqueous solution is first applied onto a tooth surface, and the other aqueous solution is subsequently applied onto the teeth surface.

3. The tooth surface treatment material according to claim 1, wherein the aqueous solution containing 2~30% by weight of a water-soluble phosphate other than a calcium salt further contains 0.0001~3% by weight of a water-soluble fluoride.

4. The tooth surface treatment material according to claim 2, wherein the aqueous solution containing 2~30% by weight of a water-soluble phosphate other than a calcium salt and an acid which does not react with the water-soluble phosphate so as not to form a compound in an amount of ½ or less of the weight of said water-soluble phosphate and having a pH of 2 or less further contains 0.0001~3% by weight of a water-soluble fluoride.

5. The tooth surface treatment material according to claim 3 or 4, wherein the water-soluble fluoride is at least one selected from a group consisting of potassium fluoride, sodium fluoride, and nickel fluoride sodium monofluorophosphate.

6. The tooth surface treatment material according to any one of claims 1 to 5, wherein the water-soluble calcium salt is at least one selected from a group consisting of calcium chloride, calcium nitrate, calcium bromide, and calcium dihydrogenphosphate.

7. The tooth surface treatment material according to any one of claims 1 to 6, wherein the water-soluble phosphate other than a calcium salt is at least one selected from a group consisting of dipotassium hydrogenphosphate, disodium hydrogenphosphate, and dilithium hydrogenphosphate.

8. The tooth surface treatment material according to any one of claims 1 to 7, wherein the acid is at least one selected from a group consisting of phosphoric acid, maleic acid, and maleic anhydride.

9. A tooth surface treatment method comprising applying an aqueous solution containing 2~30% by weight of a water-soluble calcium salt and an acid which does not react with the water-soluble calcium salt so as not to form a compound in an amount of ½ or less of the weight of the water-soluble calcium salt and having a pH of 2 or less to a tooth surface and subsequently applying another aqueous solution containing 2~30% by weight of a water-soluble phosphate other than a calcium salt to the tooth surface.

10. A tooth surface treatment method comprising applying an aqueous solution containing 2~30% by weight of a water-soluble phosphate other than a calcium salt and an acid which does not react with the water-soluble phosphate so as not to form a compound in an amount of ½ or less of the weight of the water-soluble phosphate and having a pH of 2 or less to a tooth surface and subsequently applying another aqueous solution containing 2~30% by weight of a water-soluble calcium salt to the tooth surface.

* * * * *